United States Patent [19]
Neri et al.

[11] Patent Number: 5,978,079
[45] Date of Patent: Nov. 2, 1999

[54] METHOD OF CONTROLLING THE ENDFILL OF TOBACCO ARTICLES

[75] Inventors: Armando Neri, Bologna; Maurizio Cotti, San Giovanni In Persiceto; Alberto Bonechi, Bologna, all of Italy

[73] Assignee: G.D Societa' Per Azioni, Bologna, Italy

[21] Appl. No.: 08/953,207

[22] Filed: Oct. 17, 1997

[30] Foreign Application Priority Data

Oct. 17, 1996 [IT] Italy ................................ BO96A0522

[51] Int. Cl.⁶ .................................................. G01N 21/00
[52] U.S. Cl. ........................................................ 356/237.1
[58] Field of Search ..................... 356/237.1, 445–447, 356/432, 384–387; 250/223 R, 227, 562, 578; 131/280, 94, 281, 905, 907, 908

[56] References Cited

U.S. PATENT DOCUMENTS

| | | | |
|---|---|---|---|
| 3,854,587 | 12/1974 | Mcloughlin et al. | 209/111.7 |
| 3,980,567 | 9/1976 | Benini | 250/223 |
| 4,307,963 | 12/1981 | Bolt | 356/445 |
| 5,010,904 | 4/1991 | Lassiter | 131/280 |
| 5,223,915 | 6/1993 | Neri | 356/394 |
| 5,392,359 | 2/1995 | Futamura et al. | 382/8 |
| 5,588,068 | 12/1996 | Longest et al. | 382/141 |
| 5,596,187 | 1/1997 | Di Stefano et al. | 250/222.1 |
| 5,715,843 | 2/1998 | Hapke et al. | 131/280 |

FOREIGN PATENT DOCUMENTS

| | | |
|---|---|---|
| 0434457 | 6/1991 | European Pat. Off. . |
| 0553699 | 8/1993 | European Pat. Off. . |
| 2312975 | 12/1976 | France . |
| 2149101 | 6/1985 | United Kingdom . |
| 2202628 | 9/1988 | United Kingdom . |

OTHER PUBLICATIONS

WPAT Abstract of DE 3638519, May 19, 1988.

*Primary Examiner*—Frank G. Font
*Assistant Examiner*—Michael P. Stafira
*Attorney, Agent, or Firm*—Ladas & Parry

[57] ABSTRACT

A method of controlling the endfill of elongated tobacco articles, whereby at least one collimated beam of electromagnetic radiation is directed on to a series of photosensors aligned in a direction parallel to a longitudinal axis of an article, and is partially intercepted by one end of the article; the signal emitted by each photosensor struck by the non-intercepted portion of the beam is rejected by means of a threshold measurement; and the signal emitted by each photosensor struck by the portion of the beam intercepted by and penetrating the article is compared with a range of limit values characteristic of the endfill.

10 Claims, 3 Drawing Sheets

METHOD OF CONTROLLING THE ENDFILL OF TOBACCO ARTICLES

BACKGROUND OF THE INVENTION

The present invention relates to a method of controlling the endfill of tobacco articles.

More specifically, the present invention relates to a method of controlling the endfill of cigarettes, to which the following description refers purely by way of example.

The endfill of cigarettes is normally controlled, as the cigarettes are conveyed side by side, by sensors for determining the presence of tobacco in a given end portion of each cigarette. The sensors may be capacitive, optical, inductive, etc., and are located along a path of the cigarettes, close to one end of the cigarettes. As the ends of the cigarettes are not normally aligned perfectly and are therefore variously positioned with respect to the sensors, the sensor readings are affected by the distance between the sensors and the ends being controlled.

One known solution to the problem is to correct the axial position of the cigarettes via mechanical means, such as inclined surfaces, for pushing the cigarettes into line as they are fed forward. The impact or sliding movement imposed on the cigarettes by such mechanical means, however, may result in damage to the cigarettes.

Another known solution is to determine the position of the ends of the cigarettes by means of a first optical sensor, as a succession of side by side cigarettes is fed along a given path; subject one end of each cigarette frontally to a beam of electromagnetic radiation parallel to the axis of the cigarette; and, finally, determine, by means of a second sensor, the radiation reflected by the surface of said end to generate a corresponding signal characteristic of the endfill of each cigarette.

The reading of the second sensor is corrected, taking into account the distance between the end of each cigarette and the second sensor, by means of a mathematical algorithm based on a physical model or test data; and a reject signal is generated in the event the characteristic signal is below a given threshold value.

The above front control method, however, fails to determine any cavities beneath an apparently satisfactory end surface, and involves mathematically correlating heterogeneous quantities such as the distance between the sensor and the ends of the cigarettes, and the quantity of light reflected.

SUMMARY OF THE INVENTION

It is an object of the present invention to provide a method designed to overcome the aforementioned drawbacks.

According to the present invention, there is provided a method of controlling the endfill of an end of elongated tobacco articles, each having a longitudinal axis; the method comprising the steps of directing at least one collimated beam of electromagnetic radiation, having a given emission intensity, on to a series of photosensors aligned in a first direction parallel to said axis of each article and emitting a signal proportional to an incident radiation intensity; the beam being so directed as to be partially intercepted by said end of the article; and the method being characterized by also comprising a reject step wherein the signal emitted by photosensors struck by the portion of the beam not intercepted by said end is rejected by means of a threshold measurement; and a comparing step wherein the signal emitted by photosensors struck by the portion of the beam intercepted by the article and penetrating the article is compared with a range of limit values characteristic of the end fill and a function of said emission intensity, to determine acceptability of the article.

BRIEF DESCRIPTION OF THE DRAWINGS

A number of non-limiting embodiments of the present invention will be described by way of example with reference to the accompanying drawings, in which.

DETAILED DESCRIPTION OF THE INVENTION

Figure 1:
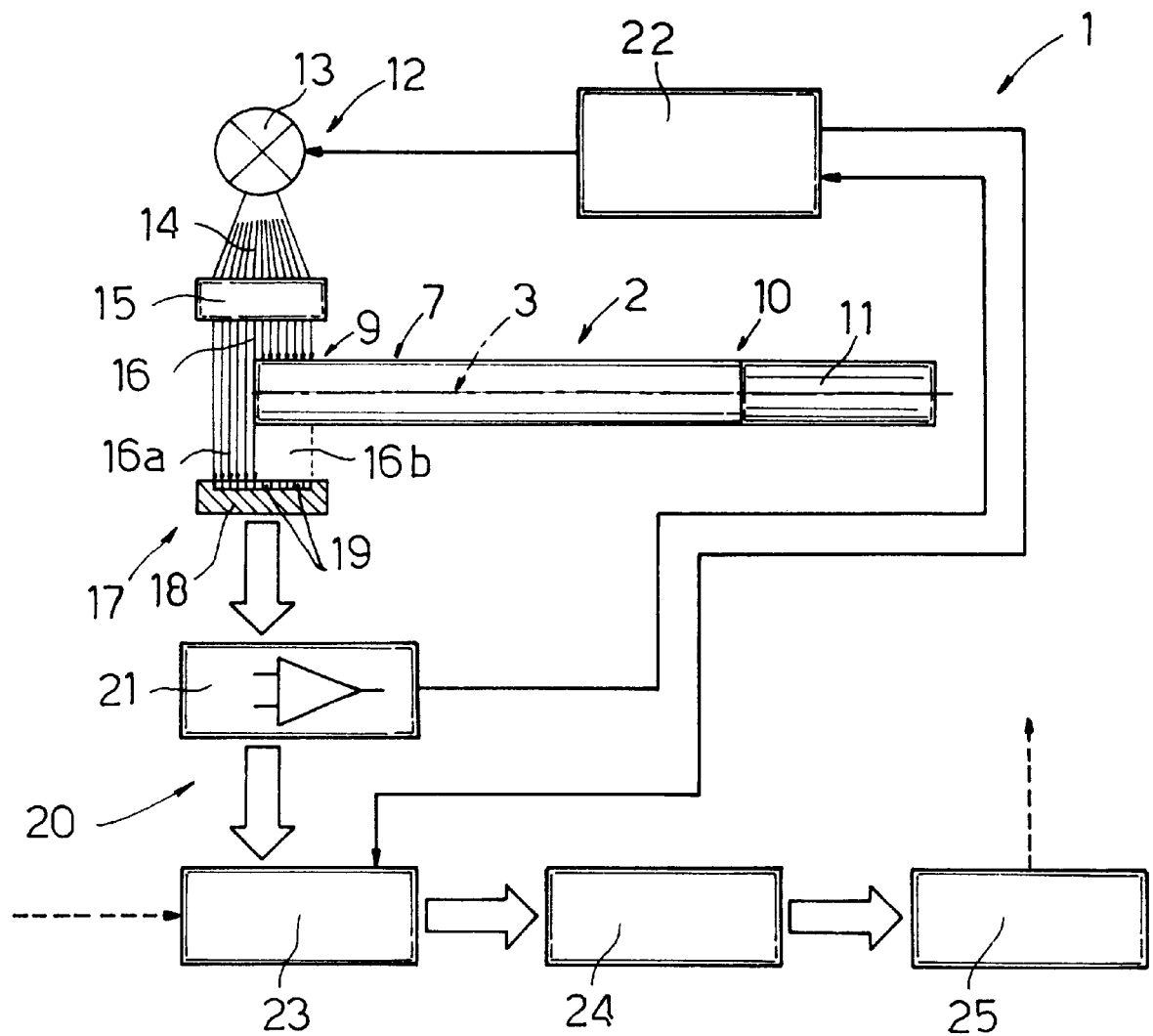
FIG. 1 shows, schematically, a preferred embodiment of a first control device implementing the method according to the present invention.

Numeral 1 in FIG. 1 indicates a device for controlling the endfill of cigarettes 2, each having a longitudinal axis 3.

Figure 2:
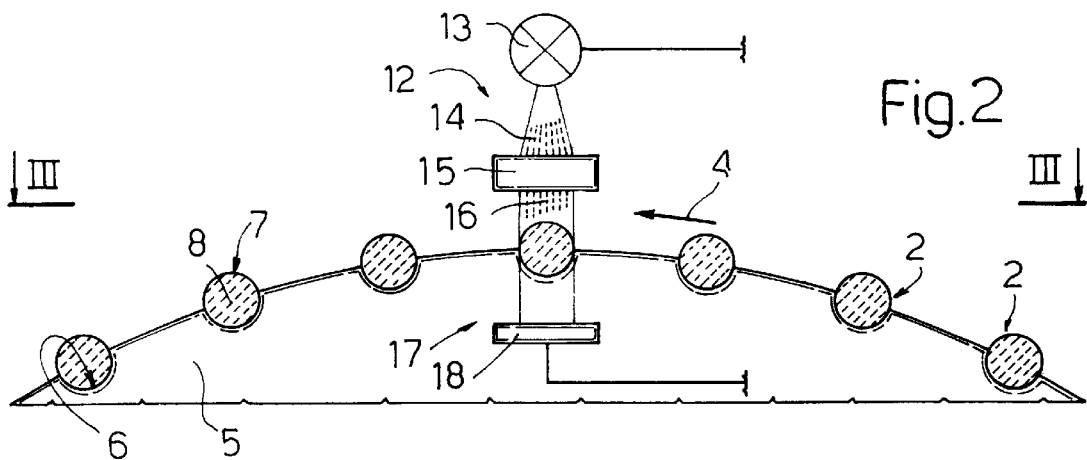
FIG. 2 shows a front view of a detail in FIG. 1.
Figure 3:
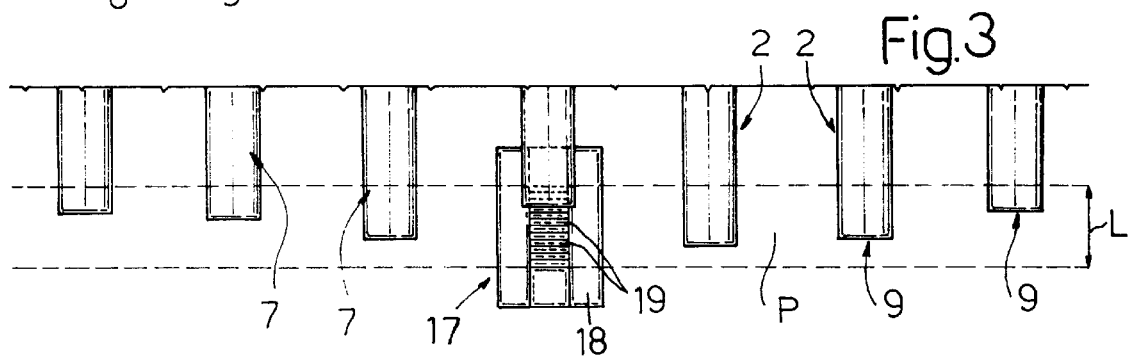
FIG. 3 shows a section along line III—III in FIG. 2.

As shown in FIGS. 2 and 3, cigarettes 2 are fed side by side in a traveling direction 4 crosswise to axis 3 by a conveying member 5, by which cigarettes 2 are retained inside respective seats 6 by known suction means (not shown).

With reference to FIGS. 1, 2 and 3, each cigarette 2 comprises a paper wrapping 7 enclosing shredded tobacco 8; a free first end 9; and a second end 10 normally comprising a filter 11. The first end 9 of each cigarette 2 projects from conveying member 5 by a length varying between a maximum and a minimum value; and the distance L between said maximum and minimum values represents the width of a path P extending in direction 4 and along which the respective ends 9 of cigarettes 2 lie. Accordingly, the path P has two, opposite longitudinal edges parallel to direction 4 representing maximum and minimum projection of the cigarette ends 9 from conveying member 5.

With reference to FIG. 1, control device 1 comprises an optical assembly 12, in turn comprising an emitter 13 for emitting a beam 14 of electromagnetic radiation, an optical collimating device 15 for forming a collimated beam 16, and a receiving assembly 17.

As shown more clearly in FIG. 3, receiving assembly 17 comprises a plate 18 supporting a series of photosensors 19 equally spaced in a direction parallel to axis 3, and each for emitting a signal proportional to the intensity of electromagnetic energy impinging on photosensor 19 itself.

Control device 1 also comprises an apparatus 20 for controlling emitter 13 and processing the signals emitted by photosensors 19, and which in turn comprises an amplifier 21 for amplifying the signals received from photosensors 19. Amplifier 21 is connected to a drive device 22 for driving emitter 13, and to a synchronizing/memorizing device 23 receiving both position signals relative to seats 6 on conveying member 5, and the signals of photosensors 19 amplified by amplifier 21; and synchronizing/memorizing device 23 is connected to an analog/digital converter 24, which transmits digitized signals to a processing unit 25 for processing a reject signal on the basis of threshold values.

In actual use, as a seat 6 on conveying member 5 nears optical assembly 12, drive device 22 activates emitter 13 to emit a beam 16, which, when collimated, is of a width at least equal to width L of path P, and extends between optical collimating device 15 and plate 18. If seat 6 contains a cigarette 2, beam 16, or a portion of it, impinges on end 9 of cigarette 2, and the collimated beam 16 is divided by end 9 into a number of components, of which will be considered, for the purpose of the control in question, a first component 16a whose energy content is unaffected by end 9, and a second component 16b which penetrates end 9 to reach plate 18. The extension, parallel to axis 3, of each component 16a, 16b depends on the position of cigarette 2, in the sense that, the further cigarette 2 projects from conveying member 5, the smaller is the extension of component 16a, which is complementary to the extension of component 16b.

Components 16a and 16b define on plate 18 a first group 19a and a second group 19b of photosensors 19.

Figure 4:
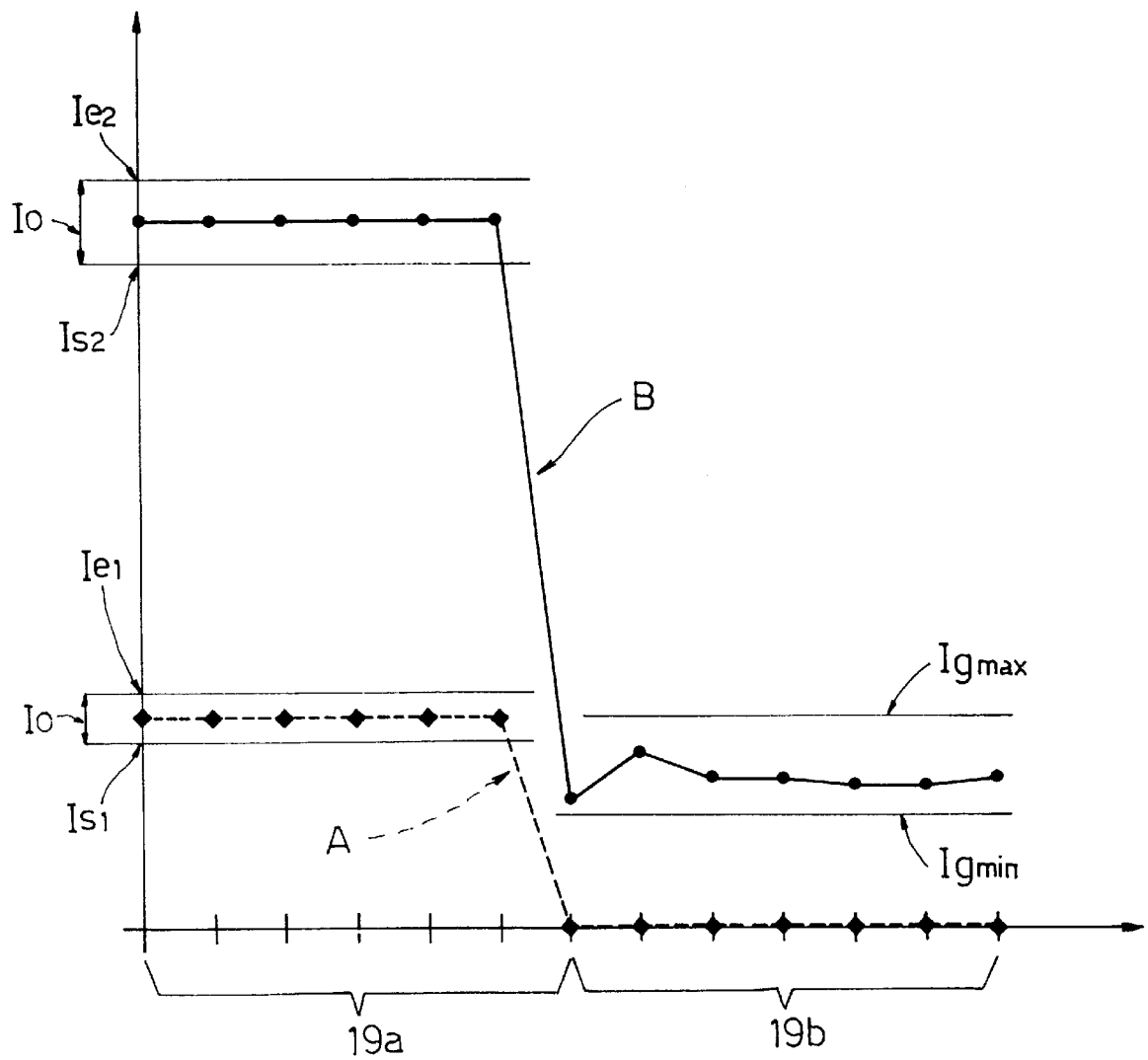
FIG. 4 shows a graph of the variation of a physical quantity determined according to the method of the present invention.

The FIG. 4 graph shows, along the Y axis, the electromagnetic energy intensity values involved; along the X axis, the position of each photosensor 19 with respect to a fixed reference point and in a direction parallel to axis 3; a first curve A showing the received energy intensity with respect to an energy intensity Ie1 emitted by emitter 13; and a second curve B showing the received energy intensity with respect to an energy intensity Ie2 emitted by emitter 13.

Due to the presence of end 9 intercepting collimated beam 16, each curve A and B shows a sharp variation in received energy intensity values Ie, which provides for distinguishing first group 19a from second group 19b of photosensors 19. Given the position of photosensors 19 along plate 18, it is therefore possible to determine the position of cigarette 2 with respect to plate 18 and/or to path P and/or to any other reference point.

The electromagnetic energy intensity values detected by sensors 19 in first group 19a substantially correspond with value Ie of the electromagnetic energy intensity emitted by emitter 13 and are equal to one another; whereas the electromagnetic energy values detected by sensors 19 in second group 19b are well below the emitted energy values, due to part of the energy being absorbed, partly refracted and partly reflected, and only a portion of the energy being transmitted through end 9 of cigarette 2.

The signals emitted by photosensors 19 in group 19b are characteristic of the endfill of end 9, and may assume different values due to nonuniformity of the filling along axis 3 of cigarette 2.

The signal emitted by each photosensor 19 is compared with a limit value Is equal to emitted energy intensity value Ie minus a value Io comprising a first component corresponding to the quantity of energy subtracted by optical collimating device 15, and a second component corresponding to a safety value. In other words, value Is is slightly below value Ie of the energy intensity emitted by emitter 13.

For each curve A and B, FIG. 4 shows the respective emitted energy intensity values Ie1, Ie2 and respective values Is1, Is2.

The signals emitted by photosensors 19 in group 19a are rejected, whereas each of the signals emitted by photosensors 19 in group 19b, if other than zero, is compared with a range of threshold values Igmin and Igmax characteristic of the endfill, to determine the acceptability of the endfill of each end 9.

Endfill threshold values Igmin and Igmax may be established experimentally for different types of shredded tobacco 8, for different types of wrappings 7, and for different emitted electromagnetic intensity values, or may conveniently be established by defining a range about a mean value detected by photosensors 19 in second group 19b relative to a given emission intensity Ie and a large number of cigarettes.

FIG. 4 shows threshold values Igmin and Igmax relative to emitted energy intensity value Ie2.

If, when controlling a cigarette 2, the signals below limit value Is are also outside the Igmin-Igmax range, a reject signal is generated relative to cigarette 2, which is subsequently rejected.

In the method described, the position of cigarettes 2 in no way affects detection of the endfill, by only the values transmitted through ends 9 being compared with the Igmin-Igmax range, with no need to correlate a cigarette 2 position signal with a characteristic endfill signal by means of special algorithms.

However, if necessary, the position of cigarettes 2 with respect, for example, to a photosensor 19 located at the end of plate 18 may be determined by simply subtracting from the segment defined by the two photosensors 19 at opposite ends of plate 18 the sum of the distances between the adjacent photosensors 19 emitting respective signals greater than or equal to the respective characteristic position value Is.

A single series of signals emitted by photosensors 19 therefore provides for obtaining information relative to both the position of cigarettes 2 and the endfill of ends 9 of cigarettes 2.

According to a preferred operating mode, drive device 22 activates emitter 13 so as to initially emit a low energy intensity Ie, and, depending on the signals emitted by photosensors 19, increases emitted energy intensity Ie if an end 9 of a cigarette 2 is detected, and cuts off emission in the absence of end 9.

Normally, low energy intensity Ie1 corresponds to curve A in FIG. 4, in which the intensity of the signals emitted by photosensors 19 in group 19b equals or is close to zero, due to the emitted energy Ie1 being practically entirely reflected or absorbed by end 9 of cigarette 2. In this first phase, it is possible to determine the position of end 9 and distinguish first group 19a from second group 19b of photosensors 19; following which, emitted energy Ie is increased to a value Ie2 to obtain signals of other than zero from photosensors 19 in group 19b. In other words, the control cycle of each cigarette 2 provides for emitting an electromagnetic energy intensity Ie ranging between a minimum initial value and a maximum value.

It is important that the maximum energy intensity value be limited to the minimum required to obtain signals of other than zero from photosensors 19 in group 19b, in that high electromagnetic radiation intensities impinging on photosensors 19 may possibly distort the signals emitted by the photosensors.

So doing not only avoids high energy being used in the absence of cigarettes 2, but also provides for adapting operation of device 1 to different brands of cigarettes 2, possibly characterized by different types of shredded tobacco 8 and different types of wrapping 7, both having different spectrophotometric characteristics.

Figure 5:
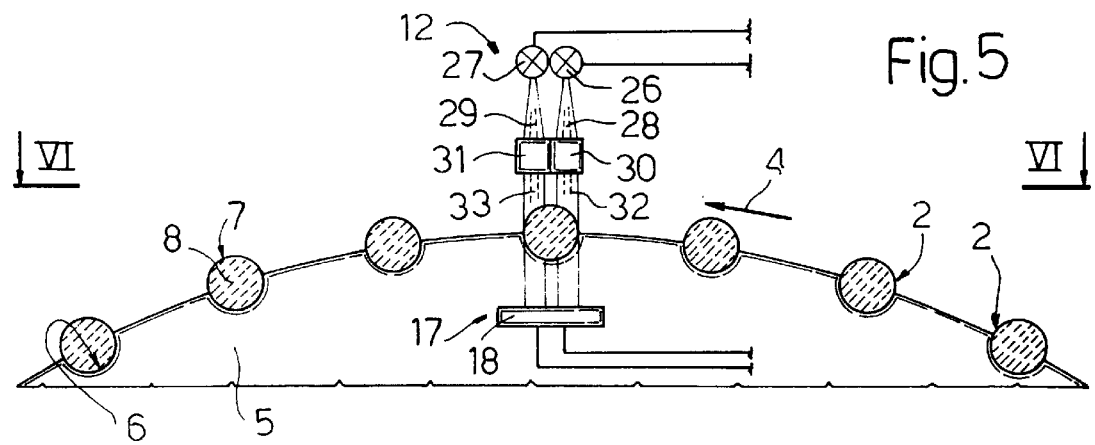
FIG. 5 shows a front view of a variation of the FIG. 2 detail.
Figure 6:
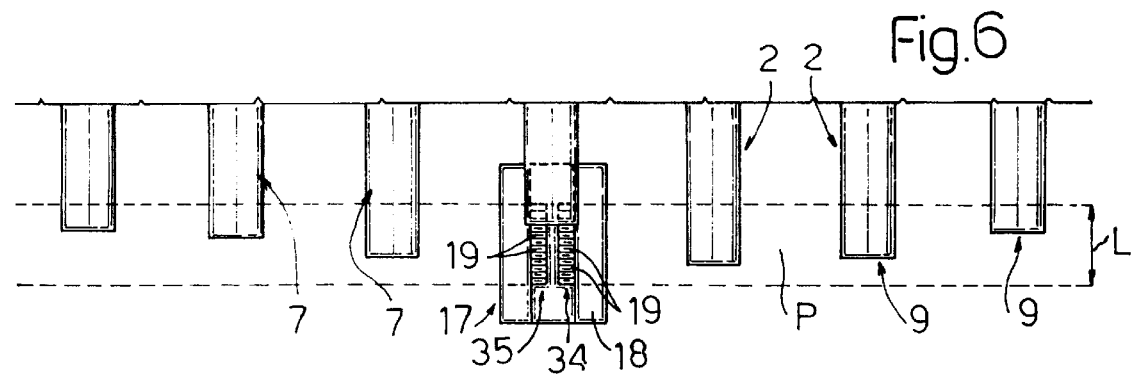
FIG. 6 shows a section along line VI—VI in FIG. 5.

In the FIGS. 5 and 6 variation, assembly 12 comprises a first emitter 26 and a second emitter 27 located side by side in the traveling direction 4 of cigarettes 2, and generating respective electromagnet radiation beams 28 and 29 through respective optical collimation devices 30 and 31 to form respective collimated beams 32 and 33; and, similarly, plate 18 is fitted with two rows 34 and 35 of photosensors 19, located side by side and for intercepting respective collimated beams 32 and 33.

In actual use, emitters 26 and 27 generate respective beams 28 and 29 of different intensities, the first emitter 26 operating at minimum intensity, and the second emitter 27 at maximum intensity.

In this alternative solution, the control cycle is performed using two collimated beams 32 and 33; a first beam 32 being detected by a first row 34 of photosensors 19 of relatively high sensitivity; and a second beam 33 being detected by a second row 35 of photosensors 19 of relatively low sensitivity.

Two collimated beams 32 and 33 may be used to advantage for controlling the endfill of particular cigarettes 2 of low radiation transparency and requiring the use of particularly high radiation intensities, which may blind photosensors 19 and, on account of the hysteresis of photosensors 19, slow down the control cycle, thus requiring a reduction in the traveling speed of cigarettes 2 in direction 4.

To safeguard the operator, radiation in the infrared spectrum is preferred.

The method described may obviously also be used in conjunction with other known control methods, such as frontal inspection of ends 9.

what is claimed is:

1. A method of controlling the endfill of an end (9) of elongated tobacco articles (2), each having a longitudinal axis (3); the method comprising the steps of directing at least one collimated beam (16; 32, 33) of electromagnetic radiation, having a given emission intensity (Ie), on to a series of photosensors (19) aligned in a first direction parallel to said axis (3) of each article (2) and emitting a signal proportional to an incident radiation intensity; the collimated beam (16; 32, 33) being so directed as to be partially intercepted by said end (9) of the article (2); a reject step wherein the signal emitted by photosensors (19) struck by the portion of the collimated beam (16; 32, 33) not intercepted by said end is rejected by means of a threshold measurement; a comparing step wherein the signal emitted by photosensors (19) struck by the portion of the collimated beam (16; 32, 33) intercepted by the article (2) and penetrating the article (2) is compared with a range of limit values (Igmin, Igmax) characteristic of the end fill and a function of said emission intensity (Ie), to determine acceptability of the article (3); and the step of feeding a succession of said articles (2), by a conveying member (5), side by side in a second direction (4) crosswise to said first direction, so that said end (9) of each article (2) is maintained along a path (P) having a given width (L) and extending through said collimated beam (16; 32, 33), which is of a width, measured in said first direction, at least equal to said given width (L), the ends (9) of the articles projecting from the conveying member (5) by a length varying between a maximum value and a minimum value, defining two opposite longitudinal edges of said path (P) parallel to said second direction (4) and spaced apart by said width (L); said collimated beam (16; 32, 33) and said series of photosensors (19) extending in said first direction across at least the entire width (L) of said path (P) between said two edges.

2. A method as claimed in claim 1, characterized in that said collimated beam (16; 32, 33) is directed in a third direction substantially perpendicular to said first and said second direction (4).

3. A method as claimed in claim 1, characterized in that said reject step comprises the substeps of comparing the signal emitted by each photosensor (19) with a limit value (Is) proportional to said emission intensity (Ie) minus a value (Io) comprising a first component proportional to a dispersed energy, and a second component corresponding to a safety value; and determining whether each signal below said limit value (Is) is within said range of limit values (Igmin, Igmax).

4. A method as claimed in claim 1, characterized in that said electromagnetic radiation is emitted by at least one emitter (13; 26, 27); and in that said emission intensity (Ie) is varied between an initial minimum intensity value (Ie1) and a maximum intensity value (Ie2).

5. A method as claimed in claim 4, characterized in that the radiation of minimum intensity (Ie1) and the radiation of maximum intensity (Ie2) are emitted respectively by a first (26) and second (27) emitter for respectively emitting a first (28) and second (29) collimated beam.

6. A method as claimed in claim 5, characterized in that said first and said second collimated beam (28, 29) are intercepted respectively by a first (34) and a second (35) row of said photosensors (19).

7. A method as claimed in claim 3, characterized by comprising the step of determining the position of said article (2) with respect to a first end photosensor (19) in said series of photosensors (19) by determining the difference between a first distance equal to the length of said series of photosensors (19), and a distance equal to the sum of the distances between the adjacent photosensors (19) emitting respective signals greater than or equal to said limit value (Is).

8. A method as claimed in claim 3, characterized by comprising the further step of emitting a signal indicating the absence of said article (2) if the signals emitted by all the photosensors (19) are greater than or equal to said limit value (Is).

9. A method as claimed in claim 1, characterized in that said electromagnetic radiation is infrared radiation.

10. A method as claimed in claim 3, characterized by comprising the further step of generating a reject signal if the value of the signal emitted by at least one photosensor (19) is below said limit value (Is) and outside said range of limit values (Igmin, Igmax).

* * * * *

UNITED STATES PATENT AND TRADEMARK OFFICE
CERTIFICATE OF CORRECTION

PATENT NO. : 5,978,079
DATED : November 2, 1999
INVENTOR(S) : Armando Neri, Maurizio Cotti, Alberto Bonechi It is certified that error appears in the above-identified patent and that said Letters Patent is hereby corrected as shown below:

On the Title Page, Item 30, "17" should read -- 18 --.

Signed and Sealed this

Twenty-sixth Day of September, 2000

Attest:

Q. TODD DICKINSON

*Attesting Officer*  *Director of Patents and Trademarks*